(12) United States Patent
Schmidt et al.

(10) Patent No.: US 7,391,949 B2
(45) Date of Patent: Jun. 24, 2008

(54) LOW LOSS HOLLOW CORE OPTICAL WAVEGUIDE

(75) Inventors: Holger Schmidt, Capitola, CA (US); Aaron Roe Hawkins, Provo, UT (US)

(73) Assignees: The Regents of the University of California, Oakland, CA (US); Brigham Young University, Provo, UT (US)

( * ) Notice: Subject to any disclaimer, the term of this patent is extended or adjusted under 35 U.S.C. 154(b) by 0 days.

(21) Appl. No.: 11/540,239

(22) Filed: Sep. 27, 2006

(65) Prior Publication Data

US 2007/0122097 A1    May 31, 2007

Related U.S. Application Data

(60) Provisional application No. 60/720,746, filed on Sep. 27, 2005.

(51) Int. Cl.
*G02B 6/10* (2006.01)
(52) U.S. Cl. .................. 385/132; 385/14; 385/125; 385/129; 385/130; 385/131; 385/141
(58) Field of Classification Search .................. 385/14, 385/125, 129, 131, 132, 141
See application file for complete search history.

(56) References Cited

U.S. PATENT DOCUMENTS 5,343,542 A * 8/1994 Kash et al. ..................... 385/31
6,542,231 B1 * 4/2003 Garrett ......................... 356/246
2002/0164547 A1 * 11/2002 Ferm et al. .................. 430/321
2004/0252957 A1 12/2004 Schmidt et al. ............. 385/131

OTHER PUBLICATIONS

"Hollow-Core Waveguides and 2-D Waveguide Arrays for Integrated Optics of Gases and Liquids," IEEE Journal of selected topics in quantum electronics, vol. 11, No. 2, Mar./Apr. 2005.*
"Integrated ARROW waveguides with hollow cores," Optics Express 2710, Jun. 14, 2004/ vol. 12, No. 12.*
"Design of a Scanning Laser Optical trap for Multiparticle Manipulation," Review of Scientific Instruments, vol. 71, No. 5, May 2000.*

* cited by examiner

*Primary Examiner*—Brian Healy
*Assistant Examiner*—Hung Lam
(74) *Attorney, Agent, or Firm*—Woodcock Washburn LLP

(57) ABSTRACT

An optical waveguide is constructed so as to comprise a non-solid core surrounded by a solid-state material. The non-solid core has an index of refraction which is lower than the index of refraction of the surrounding solid state material, and light can be transmitted with a low loss through the non-solid core. The non-solid core can extend through at least one of multiple layers of the solid state material, wherein the non-solid core is elevated on a substrate material above at least one topmost layer of the multiple solid state layers lateral to the non-solid core. In an exemplary application, the non-solid core comprises a sample material whose light transmission, absorption, and/or interference characteristics are to be measured.

54 Claims, 5 Drawing Sheets

LOW LOSS HOLLOW CORE OPTICAL WAVEGUIDE

CROSS REFERENCE TO RELATED APPLICATION

This application claims the benefit of U.S. Provisional Application No. 60/720,746, filed Sep. 27, 2005, "Low Loss Hollow Core Optical Waveguide", which is hereby incorporated by reference in its entirety.

TECHNICAL FIELD

The present invention relates generally to the field of integrated optics, and more particularly to an optical waveguide comprising a non-solid core layer surrounded by a solid-state material, wherein light can be transmitted with low loss through the non-solid core layer. A presently preferred implementation of the invention employs anti-resonant reflecting optical waveguides, known as ARROW waveguides.

BACKGROUND

The present invention improves upon the loss characteristics of an optical waveguide and related measurement system of the kind described in U.S. patent application Ser. No. 10/868,475, filed Jun. 15, 2004, "Apparatus For Optical Measurements On Low-Index Non-Solid Materials Based On Arrow Waveguides", which is hereby incorporated by reference in its entirety. This application was published on Dec. 16, 2004, with Publication Number US20040252957A1.

SUMMARY

The general field of the invention is that of integrated optical waveguides and devices. The previous application, cited above, described a method to produce integrated waveguides and arrays thereof that had hollow cores and could be built in a bottom-up integrated process. The present application describes a method and device that build on the subject matter described in the prior application but provides an improvement in waveguide performance, particularly with respect to loss. A principle aspect of the improved waveguide is that the waveguide is built upon an elevated section, or pedestal, of the substrate. This principle is shown most clearly in FIG. 2(c) of the drawings. The previous application, cited above, described structures as shown in FIG. 1(a). In both cases, all layers that would constitute the waveguide are deposited on a substrate such as silicon (Si) or glass. In the previous application, the substrate itself was not described, in connection with the illustrative embodiments, as being structured in the manner described herein. As a result, the hollow core in the center was clad horizontally by all the layers that were deposited on the substrate as well, meaning that the last lateral layer could be silicon dioxide ($SiO_2$), which is less desirable for good optical performance.

Here, we describe a method to recess the top lateral layers below the hollow core by introducing another step in the fabrication process. An initial photolithography and etching step on the underlying substrate may be used to achieve this recess and ensure that the last cladding layer in the horizontal direction is air. This is believed to improve the loss by up to one order of magnitude (see the graphs depicted in FIGS. 1(b) and 3). An implementation of this initial substrate etch step is shown in FIG. 2b.

In sum, the present application describes a way to improve hollow-core waveguide properties by initial structuring of the substrate material. An embodiment of an improved waveguide may be described as follows: A substrate is provided. The substrate may be composed of Si or glass but is not limited to these materials. For example, the substrate may be made of a semiconductor, e.g., Si or gallium arsenide, or an insulator, e.g., quartz glass, pyrex, etc. The substrate is generally planar but is elevated in the areas underlying the hollow core of the waveguide, as depicted in FIG. 1(c). The substrate is preferably etched at the beginning of the fabrication process to form a pedestal of depth $d_e$ on top of which the ARROW fabrication process is carried out. As a result, all layers are recessed by $d_e$ and if $d_e$ is equal to or larger than the thickness of all layers on top of the core, the hollow core will be surrounded by air on three of four sides, resulting in strongly improved waveguide loss. The ARROW layers are formed by dielectric layers of varying index. For example, as shown in FIG. 1(c), the waveguide region of the structure is provided by forming alternating layers of high-index dielectric cladding materials, which are denoted in FIG. 1(c) by the reference signs $n_1$, $n_2$, which refer to their respective indices of refraction. The cladding layers may be $SiO_2$ and SiN, but are not necessarily limited to these materials. It should be noted that the 1st layer, i.e., the one closest to the substrate, may be either SiN or SiO2. That is, it is not critical to start with one or the other, although there are some subtle differences in how one calculates the thickness of the layer. SiN has been found to work better, but these could be completely different dielectrics altogether. In addition, it should be noted that an exemplary application of the inventive waveguide structure is in a measurement system having the perpendicular waveguide sections as described in U.S. patent application Ser. No. 10/868,475, filed Jun. 15, 2004, "Apparatus For Optical Measurements On Low-Index Non-Solid Materials Based On Arrow Waveguides", which has been hereby incorporated by reference. Notwithstanding this, it should be noted that the inventive structure could be advantageously applied to straight waveguides without intersections as well.

Other aspects of illustrative embodiments of the invention are described below.

BRIEF DESCRIPTION OF THE DRAWINGS

FIG. 2c schematically depicts an improved optical waveguide in accordance with the present invention.

DETAILED DESCRIPTION OF ILLUSTRATIVE EMBODIMENTS

1. Introduction

Figure 1:
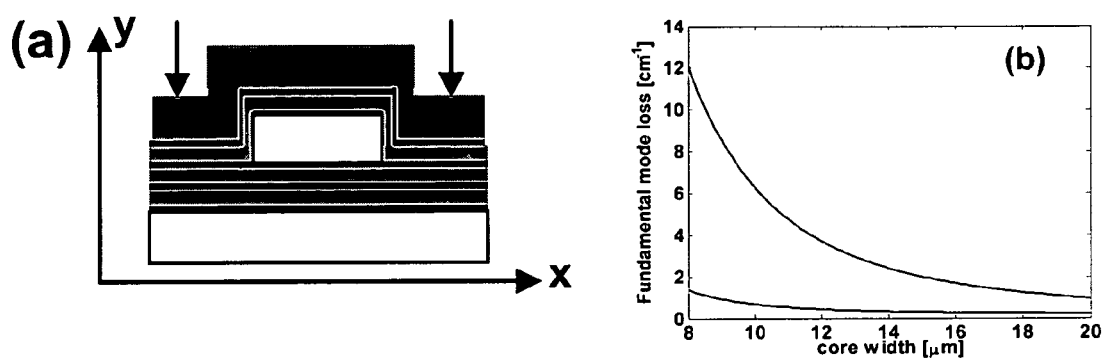
FIG. 1: a) Hollow-core ARROW waveguide cross section. b) Loss optimization as function of core width. dashed line: laterally terminating layer is $SiO_2$; solid line: laterally terminating layer is air (core height: 5.8 µm).

Optical waveguides with hollow cores have recently garnered a lot of interest. The ability to propagate light in a low-index core extends the paradigm of conventional solid-state integrated optics to non-solid core materials such as liquids and gases. Liquid cores have a tremendous potential for sensing of biological materials that are typically present in aqueous solution, in particular in combination with other components of a larger microfluidic analysis system. Air or gas-filled cores are attractive for sensor devices as well, but can also be used in other areas, including quantum optics and quantum information processing. In order to realize hollow-core waveguides, one must devise a way to confine light in a low-index medium, which has been achieved using various approaches. For liquid cores, specialized low-index claddings such as Teflon AF can be used. Dress and Franke, *Appl. Phys. B.* 63:12, 1996. (Full citations for references are provided at the end of this specification.) Confinement can also be achieved by surrounding the core with multiple high-index dielectric cladding layers. Using periodic structures such as photonic crystals (Fink et al., *Science* 282:1679, 1998) photonic crystal (holey) fibers (Russell, *Laser Focus World* 38:77, 2002), or Bragg waveguides (Hadley et al., *Opt. Lett.* 29:809, 2004), light propagation through air or gas over various distances has successfully been demonstrated. Application of such structures to practical problems has also begun. For example, quantum optical effects such as electromagnetically induced transparency and slow light were recently observed in acetylene-filled holey fiber. Ghosh et al., *Phys. Rev. Lett.* 945:093902, 2005.

Antiresonant reflecting optical waveguides (ARROWs) were recently demonstrated as an alternative way to realize hollow-core integrated optics. While also employing multiple dielectric cladding layers, ARROWs do not require periodicity to achieve low propagation loss and rely on antiresonance of the transverse wavevector component for each layer. Dugay et al., Appl. Phys. Lett. 49:13, 1986. This provides additional design flexibility that can be used to add integrated wavelength filtering or to realize interconnected two-dimensional waveguide arrays. Schmidt et al., IEEE J. of Selected Topics in Quantum Electronics 11:519, 2005. Propagation in ARROWs with rectangular cores fabricated with silicon microfabrication techniques was observed using both liquid (Yin et al., Applied Physics Letters 85:3477, 2004) and air (Yin et al., Optics Express 12:2710, 2004) as the core materials. These initial results demonstrated the potential of the ARROW approach, but exhibited relatively large waveguide loss, especially for air cores.

Here, we present experimental results for strongly reduced loss in hollow-core ARROWs after modifications in the fabrication process. Additional optimization through accounting for the characteristics of rectangular core fabrication is carried out quantitatively, and an optimized design is presented. We focus on air as the core material, but the methods described here are equally applicable to liquid cores. We also present a study of the polarization dependence of light propagation in optimized hollow-core ARROWs. We discuss optimization of the optical properties of hollow-core antiresonant reflecting optical waveguides (ARROWs). We demonstrate significant reduction of waveguide loss to 2.6/cm for a 10.4 $\mu m^2$ mode area after adding an initial etching step of the substrate material. The effect of differences in confinement layer thickness is quantified and an optimized design is presented. The polarization dependence of the waveguide loss is measured.

It is to be understood that this invention is not limited to particular methods, reagents, compounds, or compositions, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a layer of solid state material" includes a combination of two or more layers of solid state material, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

2. Waveguide Optimization

Fabrication of hollow-core ARROWs with rectangular cross section has been previously described. Barber et al., *IEEE Phot. Tech. Lett.* 17:363, 2005. In essence, a dielectric multilayer stack for ARROW confinement is formed by alternating deposition of $SiO_2$ and SiN layers using plasma-enhanced chemical vapor deposition (PECVD). In between top and bottom claddings, a sacrificial core layer (typically SU-8) is deposited and patterned. The final step is removal of the sacrificial layer with a suitable etch. The resulting structure is sketched in FIG. 1a.

Figure 2:
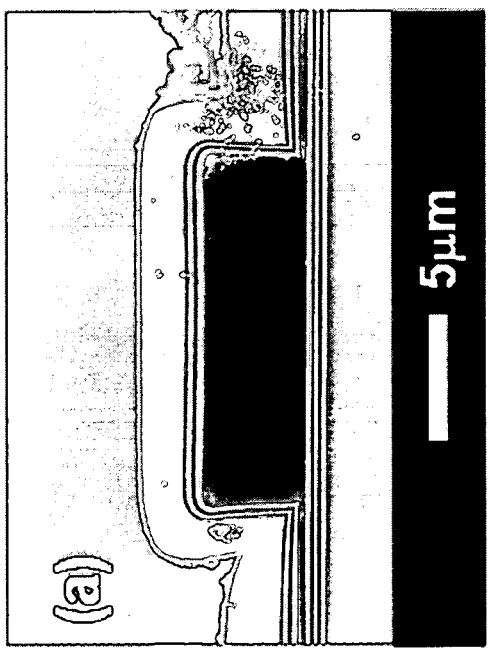
FIG. 2: SEM images of hollow-core ARROW waveguides. a) no substrate etch; b) pre-etched Si substrate (core height $d_c$=5.8 µm).
Figure 2:
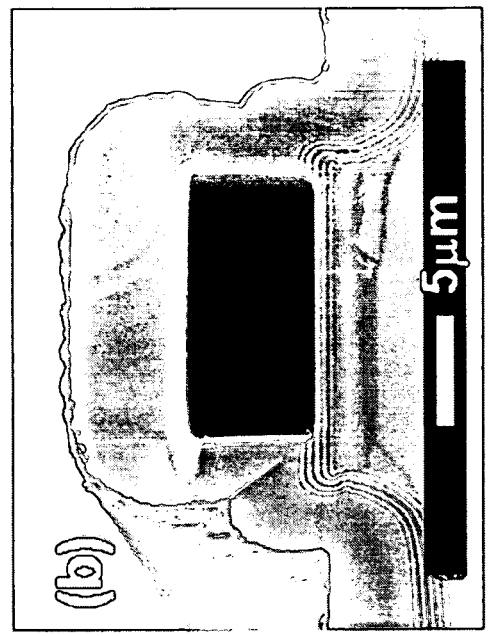
Figure 2:
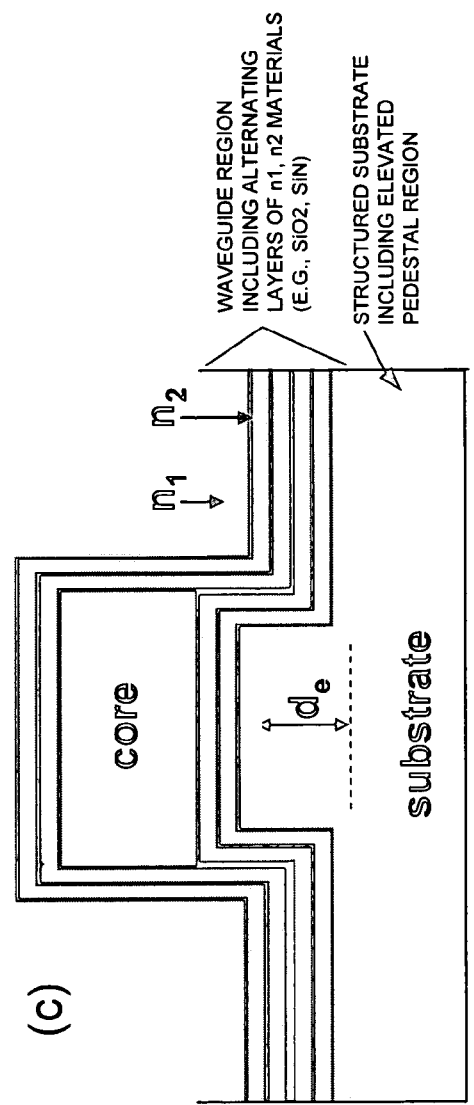

A major impediment to lowering waveguide loss results from the fact that the core is enclosed by high-index solid materials on three of four sides (Si substrate on the bottom, and $SiO_2$ in lateral direction) as indicated by the two vertical arrows in FIG. 1a. This leads to unnecessarily large values for the waveguide loss, especially for gaseous cores with index $n_c \sim 1$. The lower the index of the final lateral cladding can be made, the lower the total waveguide loss α will be. FIG. 1b illustrates this effect. The dashed line shows the α-dependence on core width w if the lateral termination is $SiO_2$ (n=1.46), and horizontally (x-direction) polarized input light at 785 nm and core index $n_c=1$ are considered. This corresponds to the situation found in previously demonstrated ARROWs (Yin et al., *Optics Express* 12:2710, 2004) where the thick top $SiO_2$ layer that provides mechanical stability to the waveguides clads most of the core laterally as a result of the PECVD deposition. This can also be seen in the SEM image in FIG. 2a.

In contrast, the solid line in FIG. 1b shows the loss for the same structure, but using air as the final index in lateral direction. Clearly, a significant reduction in loss by a factor of ~5-6 is possible. Here, all layer thicknesses were assumed to have the correct thickness to fulfill the antiresonance condition for low ARROW loss $$d_i = \frac{\lambda}{4n_i}(2N+1)\left[1 - \frac{n_c^2}{n_i^2} + \frac{\lambda^2}{4n_i^2 d_c^2}\right]^{-0.5} \quad (1)$$

where $d_i$ ($d_c$) represent ARROW layer (core) thickness, $n_i$ ($n_c$) are the cladding (core) indices, N is the antiresonance order, and $\lambda$ is the optical wavelength. We will revisit the layer thicknesses in section 3.2.

3. Results and Discussion

3.1 Waveguide Loss in Pre-Etched Structures

In order to validate the calculations shown in FIG. 1b, we fabricated waveguides where the core is terminated by air in three directions (FIG. 2b). This structure was built by pre-etching the silicon substrate before forming the ARROW waveguide. Photoresist lines were defined on the Si substrate using optical lithography, followed by a relatively isotropic $CF_4$-based RIE etch. This resulted in pedestal-like ridges on the substrate on which the ARROW process was carried out as previously described. Barber et al., *IEEE Phot. Tech. Lett.* 17:363, 2005. The SU-8 sacrificial layers were aligned with respect to the Si pedestals. As seen in FIG. 2b, the topmost thick $SiO_2$ layer is now lowered below the core level, resulting in air being the laterally terminating material. A different method for realizing recessed dielectric layers has previously been used for solid-core Bragg waveguides. Yi et al., *Optics Express* 12:4775, 2004. Waveguides with widths of 9, 12, and 15 μm were fabricated for both structures.

Figure 3:
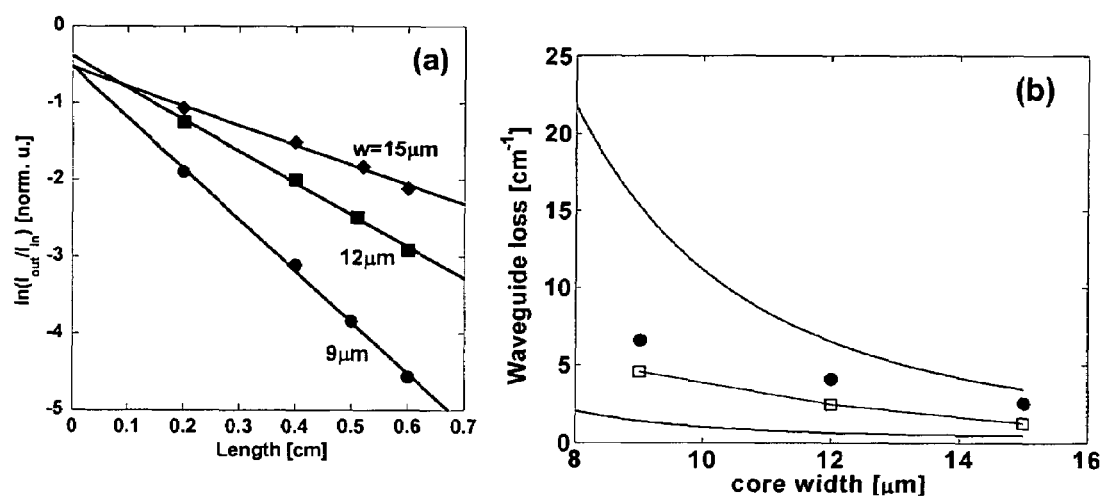
FIG. 3: a) Transmitted power versus pre-etched waveguide length (symbols: experiment, lines: exponential fits). b) Hollow-core waveguide loss versus core width; circles: experiment, squares: simulation, solid line: non-pre-etched sample (theory), dashed line: further optimization via thickness optimization (theory).

The waveguide loss was determined using the cutback method, i.e. by repeated cleaving of the waveguide and measuring the transmission versus sample length L. Light from a diode laser (P~1 mW) was end-coupled into the waveguide core through single-mode fiber, and the transmitted light was collected with a high-NA lens and focused onto a CCD detector. Fitting of the transmission curve with a mono-exponential decay yields the total waveguide loss for a given core width as shown in FIG. 3a. This number corresponds to the loss of the fundamental mode for all samples except for w=15 μm for which the contribution of the third order mode to the total loss is non-negligible.

FIG. 3b shows the dependence of the waveguide loss on the core width. The solid line shows the calculated fundamental mode loss for a waveguide without pre-etched substrate and horizontal ARROW layer thicknesses fulfilling eqn. Dress and Franke, *Appl. Phys. B.* 63:12, 1996. In comparison, the experimental results (circles) show a substantial loss reduction up to a factor of three for the narrowest cores. We observed mode loss as low as 2.6/cm for w=15 μm, and reasonable loss of 6.8/cm for w=9 μm with a mode area of only 6.25 μm². The latter value equals the loss previously measured in a much wider structure (w=24 μm, $d_c$=3.5 μm). Yin et al., *Optics Express* 12:2710, 2004. This improvement for smaller mode areas is particularly attractive for applications in nonlinear optics where effects scale with intensity. We also find very good agreement with full 2D simulations for the loss (rectangles) that took into account the non-uniformity of the $SiO_2$ thickness on the sides of the core. The remaining discrepancy between experiment and theory is likely due to surface roughness and scattering.

3.2 Layer thickness optimization

The theory values (rectangles) shown in FIG. 3b are not as low as one would expect from a perfectly optimized structure (FIG. 1b). The main reason for this discrepancy is the difference in thickness of vertical ($t_V$) and horizontal ($t_H$) cladding layers above the core. This can be seen in the SEM images in FIG. 2 and has been previously observed. Yin et al., *Optics Express* 12:2710, 2004. The effect is intrinsic to the PECVD deposition process and cannot be avoided. The fact that their thickness ratio $r=t_H/t_V \neq 1$ means that horizontal and vertical layers cannot simultaneously fulfill the antiresonance condition (eqn. (Dress and Franke, *AppL. Phys. B.* 63:12, 1996)), and the overall loss increases.

However, if r is known, the layer thicknesses can be designed to largely compensate for this mismatch. The waveguide loss can be approximated very well as a sum of the one-dimensional transverse (y) and lateral (x) losses (Schmidt et al., *IEEE J. of Selected Topics in Quantum Electronics* 11:519, 2005), and the transverse loss has a higher thickness tolerance due to its TE character. Therefore, the design strategy is to reduce the overall loss by deliberate deviation from the optimum thickness above the core. Using this strategy, the calculated loss can be brought empirically within ~10 percent of the value expected for an ideal structure. We point out that a further constraint for air-core waveguides arises from the fact that the first layer adjacent to the air core should ideally have a value of $t_V=2t_H$ for low-loss propagation. This is a result of the TM character of x-polarized light with respect to the vertical cladding and the fact that the fundamental mode propagates at an angle exceeding the Brewster angle. Hadley et al., *Opt. Lett.* 29:809, 2004.

We used high-resolution SEM images to determine r for the pre-etched waveguides shown in FIG. 2b. We found r=1.45±0.05 for the thinner SiN and $SiO_2$ layers closer to the core, and r=1.59±0.01 for the upper part of the outermost thick $SiO_2$ layer. It is best to calibrate the r-values separately for thick (>1 μm) and thin (<1 μm) layers for the desired core cross section and PECVD growth conditions. Based on the measured values, we designed an optimized structure for the same core dimensions as in FIG. 2b ($d_c$=5.8 μm). The first step is to minimize the loss by varying the thickness of the outermost $SiO_2$ layer while assuming ideal values for all other layers. Subsequently, the thin layers are sequentially optimized starting with the first SiN layer adjacent to the core and moving towards the outside. The optimized structure has the following layer sequence above the core (all values in nm): SiN (90), $SiO_2$ (195), SiN (134), $SiO_2$ (198), SiN (106), $SiO_2$ (3900). We see that the thicknesses differ from the original design (106/184 nm) as expected. The calculated waveguide loss for this optimized structure that combines both pre-etched substrate and optimized thickness design is shown as the dashed line in FIG. 3b. We see that significant further improvement in the waveguide loss is possible.

Figure 4:
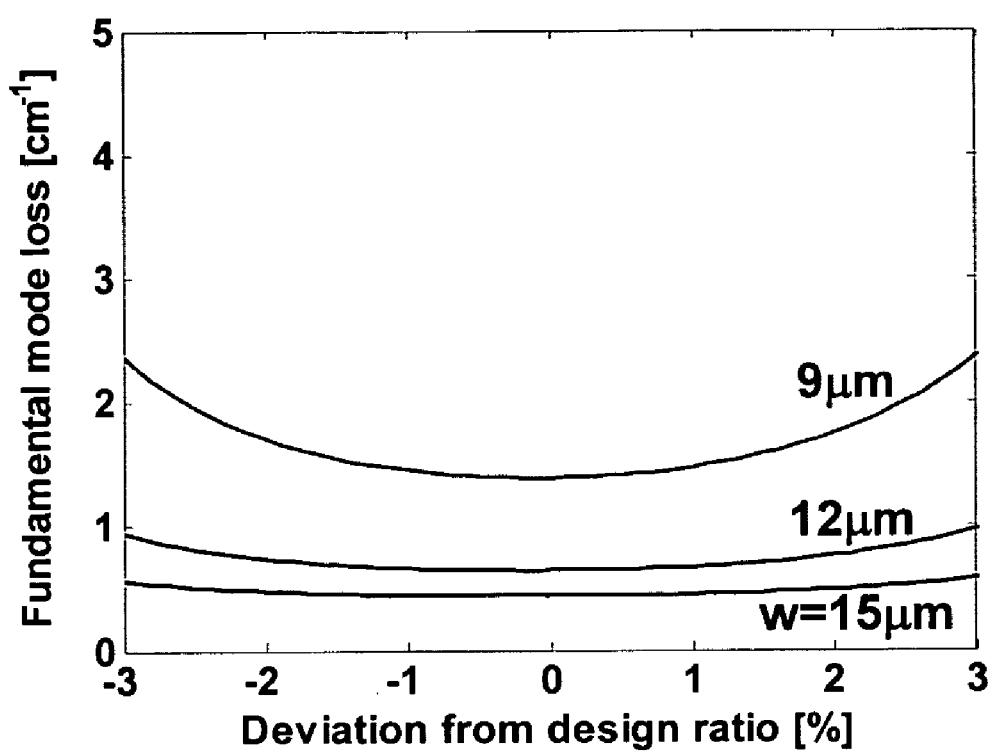
FIG. 4: Calculated waveguide loss versus deviation of ARROW layer thickness ratio r from design value for various core widths.

Given the fact that the loss is very sensitive to r, we analyzed the effect of deviations from the design r-value on the waveguide loss. The results are shown in FIG. 4 for three core widths over a deviation range that is well within the accuracy of a PECVD system. We see that the loss increases by ≦1/cm for deviations ≦3%. It is important to note, however, that large r deviations, e.g. the lateral protrusions in the outermost $SiO_2$ layer as seen in FIG. 2b, affect the waveguide loss more strongly. This variation is due to the non-vertical etch profile and can be corrected by an RIE etch process that produces deeper and more vertical sidewalls.

3.3 Polarization Dependence

It has been known since the first demonstration of solid-core ARROW waveguides with one-dimensional confinement (Dugay et al., *Appl. Phys. Lett.* 49:13, 1986) that the propagation loss has a very strong dependence on the polarization of the incident light. Due to the difference in reflection coefficients from a dielectric layer (Yeh, *Wiley Interscience,*

1998), p-polarized waves experience much higher loss than s-waves. In a two-dimensional rectangular waveguide, incident x-polarization corresponds to a p-wave in x-direction, and an s-wave in the y-direction. In accordance with our design, it is therefore preferable to use larger core dimensions in the x-direction to achieve low loss.

Figure 5:
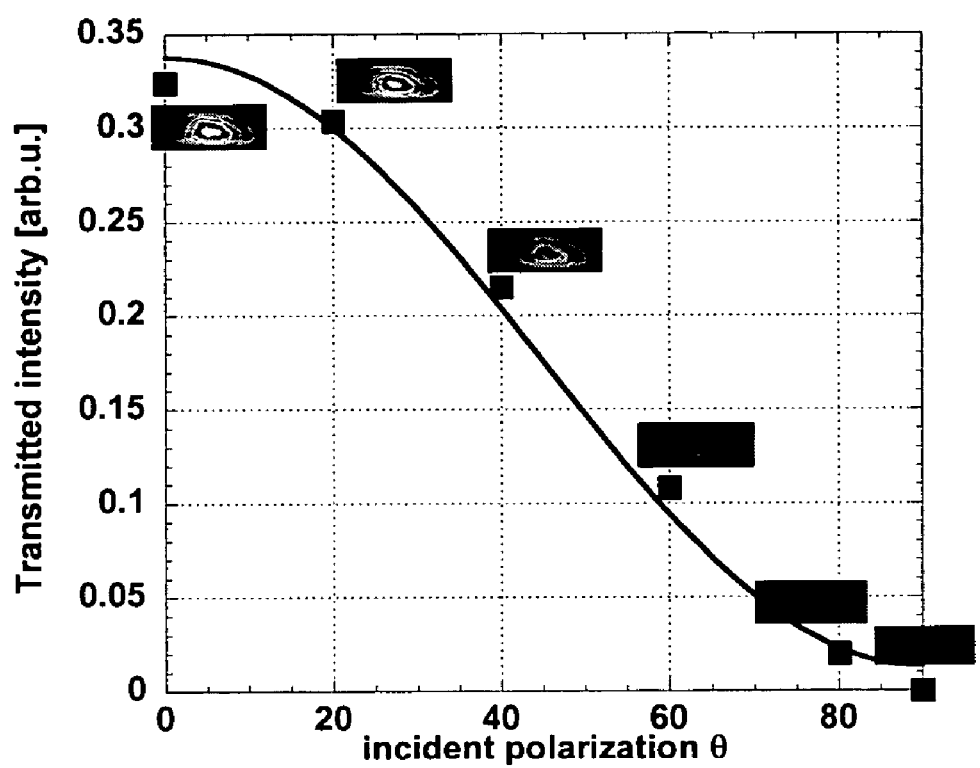
FIG. 5: Transmitted intensity and mode images versus (linear) input polarization angle for pre-etched hollow-core waveguides (w=15 µm). Symbols: experiment; line: calculated fit to equation (2).

In order to map the polarization dependence in hollow-core ARROW waveguides, we have carried out polarization dependent loss measurements. A half-wave plate was placed after the excitation source to vary the incident linear polarization angle θ continuously from x (0°) to y-polarization (90°). FIG. 5 shows the recorded output intensity (symbols) as a function of θ for the pre-etched waveguides along with mode images at different θ-values. A clear reduction in throughput as y-polarization is approached is observed. The mode image on a CCD camera vanishes completely at θ=90°. Theoretically, the output intensity $I_o$ is given by $$I_o = I_i e^{-\alpha_X L} \cos^2(\theta) + I_i e^{-\alpha_Y L} \sin^2(\theta) \qquad (2)$$

where $I_i$ is the input intensity including insertion loss, and $\alpha_X$ and $\alpha_Y$ are the waveguide losses in x and y-directions, respectively. The lines show a fit of the transmitted intensity to equation (Fink et al., Science 282:1679, 1998) that matches the data very well. The fitting parameters are the intensity values at 0° and 90°, respectively. In principle, $\alpha_Y$ can be deduced from the ratio between these two parameters for a given sample length L and the previously determined $\alpha_X$. However, the expected $\alpha_Y$ in these waveguides is extremely high (181/cm) and exceeds our background-limited upper detection limit of 20/cm. Our measurements confirm that waveguide loss in hollow-core ARROWs can be highly polarization selective.

4. Optical Tweezers

Optical tweezers provide a method to hold, direct and manipulate small particles of micron or sub-micron size such as cells or cell parts using light (Ashkin A. History of optical trapping and manipulation of small-neutral particle, atoms, and molecules. IEEE Journal of Selected Topics in Quantum Electronics, vol. 6, no. 6, November-December 2000, pp. 841-56 and references therein). This has the advantage that no mechanical interaction is present that could damage the specimen. The effect is based on light pressure, i.e., the notion that light carries with it a certain amount of momentum that can be transferred to material objects.

An optical tweezer is generally understood as being a single-beam optical trap where a laser beam is strongly focused by a high aperture lens. Two types of forces result as the beam hits a small object. One is a scattering force that pushes the object along the direction of the beam, i.e., along x. The second one is the trapping force F, which is directed along -x. If the aperture of the lens is large enough, the trapping force can dominate over the scattering force and trap a particle at a point close to the focus of the lens. No integrated version of such tweezers exists to date. By deliberately shaping (tapering) the lateral profile of an integrated ARROW waveguide with non-solid core (central tapered area), the intensity profile of a Gaussian beam can be emulated. In the same way as in traditional optical tweezers using lenses, the intensity gradient of light propagating along x will induce scattering and trapping forces on a microscopic particle inside the waveguide, leading to an integrated version of optical tweezers. Note that no lenses are required in this case and that the beam profile can be shaped and designed in ways different from profiles obtainable from bulk optics. In a particular application, this concept can be used to hold a particle at the intersection of the ARROW waveguide with another waveguide. This can facilitate optical experiments such as fluorescence studies on the sample particles.

5. Conclusion

The optical properties of hollow-core ARROW waveguides with rectangular cross section can be substantially improved by optimizing design and fabrication processes. We have shown that pre-etching of the silicon substrate results in a substantial waveguide loss reduction compared to previously published results. Loss values as low as 2.6/cm and mode areas of 6.25 μm² were observed. A quantitative analysis of the thickness difference of horizontal and vertical ARROW layers resulted in a further improved design that can lead to another three-fold loss reduction. In addition, the polarization dependence of the waveguide loss was analyzed and the polarization selectivity of hollow-core ARROWs was demonstrated.

The significantly lower loss that can be achieved in air-core ARROWs using the optimization strategies presented here makes application of these waveguides in chip-scale devices possible. Such applications include gas sensors or nonlinear optical devices based on quantum interference. Schmidt and Hawkins, Appl. Phys. Lett. 86:032106, 2005. Further improvement is feasible by improving the fabrication process or by exploring alternative, non-rectangular core shapes.

While the present invention has been described in connection with several presently preferred or illustrative embodiments, it is to be understood that other similar embodiments may be used or modifications and additions may be made to the described embodiments for performing the same functions of the present invention without deviating therefrom. For example, while exemplary embodiments of the invention are described as including ARROW waveguides, one skilled in the art will recognize that the present invention is not limited thereto, and that the methods described herein may apply to other implementations, and may be applied to any number of such devices and applications without departing from the invention. Therefore, the present invention should not be limited to any single embodiment, but rather should be construed in breadth and scope in accordance with the appended claims.

What is claimed:

1. An optical waveguide, comprising a substrate made of a solid material and multiple layers of solid state material disposed on the substrate, and a non-solid core extending through at least one of said multiple layers, wherein said non-solid core is elevated on said substrate on a pedestal-like ridge above one topmost layer of said multiple layers lateral to said non-solid core, and whereby said non-solid core may be used to contain a sample material whose light transmission, absorption, or interference characteristics are to be measured.

2. An optical waveguide as recited in claim 1, wherein said substrate is recessed lateral to said non-solid core.

3. An optical waveguide as recited in claim 1, wherein said substrate comprises Silicon (Si) and said multiple layers include $SiO_2$ and SiN.

4. An optical waveguide as recited in claim 3, wherein said non-solid core has an index of refraction which is lower than the index of refraction of the surrounding solid-state material, and wherein light can be transmitted with low loss through the non-solid core.

5. An optical waveguide as recited in claim 1, wherein said optical waveguide is generally structured as an anti-resonant reflecting optical waveguide (ARROW).

6. An optical waveguide as recited in claim 1, comprising a antiresonant reflecting layers adjacent to said non-solid core, whereby light is substantially prevented from leaking out of said core in a transverse direction.

7. An optical waveguide as recited in claim 1, further comprising a perpendicular waveguide portion for use in injecting light into said non-solid core for measuring fluorescence characteristics associated with the sample material.

8. An optical waveguide as recited in claim 1, wherein the non-solid core has a substantially square cross-section.

9. An optical waveguide as recited in claim 1, wherein the non-solid core has a substantially rectangular cross-section.

10. An optical waveguide as recited in claim 1, wherein the non-solid core has a substantially semicircular cross-section.

11. An optical waveguide as recited in claim 1, further comprising a sample-injection port for injecting a fluid into said non-solid core, said sample injection port being oriented substantially perpendicularly with respect to a longitudinal axis of said non-solid core.

12. An optical waveguide as recited in claim 1, wherein said substrate comprises a semiconductor material.

13. An optical waveguide as recited in claim 1, wherein said substrate comprises a metal.

14. An optical waveguide as recited in claim 1, wherein said substrate comprises a plastic.

15. An optical waveguide as recited in claim 1, wherein said substrate comprises a polymer.

16. An optical waveguide as recited in claim 1, wherein said substrate comprises a silicon based glass.

17. An optical waveguide as recited in claim 1, wherein said substrate comprises alumina.

18. An optical waveguide as recited in claim 1, wherein said substrate comprises sapphire.

19. An optical waveguide as recited in claim 1, wherein the layer of solid state material through which said non-solid core extends comprises a material deposited by chemical vapor deposition.

20. An optical waveguide as recited in claim 1, wherein the layer of solid state material through which said non-solid core extends comprises silicon oxy-nitride.

21. An optical waveguide as recited in claim 1, wherein the layer of solid state material through which said non-solid core extends comprises a material sputtered onto said substrate.

22. An optical waveguide as recited in claim 1, wherein the layer of solid state material through which said non-solid core extends comprises a material evaporated onto said substrate.

23. An optical waveguide as recited in claim 1, wherein the layer of solid state material through which said non-solid core extends comprises silicon dioxide.

24. An optical waveguide as recited in claim 1, wherein the layer of solid state material through which said non-solid core extends comprises silicon nitride.

25. An optical waveguide as recited in claim 1, wherein the layer of solid state material through which said non-solid core extends comprises a material spun-on said substrate.

26. An optical waveguide as recited in claim 1, wherein the layer of solid state material through which said non-solid core extends comprises a material dip coated onto said substrate.

27. An optical waveguide as recited in claim 1, wherein the waveguide is made using a sacrificial layer material comprising a metal.

28. An optical waveguide as recited in claim 1, wherein the waveguide is made using a sacrificial layer material comprising a polymer.

29. An optical waveguide generally structured as an antiresonant reflecting optical waveguide (ARROW), comprising:
    a substrate and multiple layers of solid state material, including SiO$_2$ and SiN, disposed on the substrate, and a non-solid core extending through at least one of said multiple layers, wherein said non-solid core is elevated on said substrate on a pedestal-like ridge above one topmost layer of said multiple layers lateral to said non-solid core, and wherein said non-solid core has an index of refraction which is lower than the index of refraction of the surrounding solid-state material, and wherein light can be transmitted with low loss through the non-solid core;
    a Fabry-Perot reflector adjacent to said non-solid core, for substantially preventing light from leaking out of said core in a transverse direction;
    a perpendicular waveguide portion for use in injecting light into said non-solid core for measuring fluorescence characteristics associated with the sample material; and
    a sample-injection port for injecting a fluid into said non-solid core, said sample injection port being oriented substantially perpendicularly with respect to a longitudinal axis of said non-solid core;
    whereby said non-solid core may be used to contain a sample material whose light transmission, absorption, or interference characteristics are to be measured.

30. An optical waveguide as recited in claim 29, wherein said substrate is recessed lateral to said non-solid core.

31. An optical waveguide as recited in claim 29, wherein the non-solid core has a substantially square cross-section.

32. An optical waveguide as recited in claim 29, wherein the non-solid core has a substantially rectangular cross-section.

33. An optical waveguide as recited in claim 29, wherein the non-solid core has a substantially semicircular cross-section.

34. An optical measurement system, comprising:
    (a) an optical waveguide comprising a channel surrounded by a solid-state material, including a Fabry-Perot reflector adjacent to said channel, whereby light is substantially prevented from leaking out of said channel in a transverse direction; and wherein said channel is elevated on a substrate on a pedestal-like ridge above one topmost layer of said solid state material lateral to said channel;
    (b) means for injecting into said channel a sample material having an index of refraction which is lower than the index of refraction of the surrounding solid-state material;
    (c) means for injecting light into said channel, wherein the injected light is guided within the channel and through the sample material;
    (d) a perpendicular waveguide portion for use in injecting light into the channel; and
    (e) means for measuring selected optical properties associated with the sample.

35. A system as recited in claim 34, wherein said selected optical properties include transmission, absorption, interference or fluorescence characteristics associated with said sample material over macroscopic distances within the channel.

36. A system as recited in claim 34, wherein the channel has a length which is optimized for a desired range of wavelengths.

37. A system as recited in claim 34, wherein said optical waveguide comprises a silicon (Si) substrate and multiple layers of solid state material disposed on the substrate, and a non-solid core extending through at least one of said multiple layers, whereby said non-solid core may be used to contain the sample material.

38. A system as recited in claim 37, wherein said substrate is recessed lateral to said non-solid core.

39. A system as recited in claim 37, wherein said multiple layers include $SiO_2$ and SiN.

40. A system as recited in claim 34, wherein said non-solid core has an index of refraction which is lower than the index of refraction of the surrounding solid-state material, and wherein light can be transmitted with low loss through the non-solid core.

41. A system as recited in claim 34, wherein said optical waveguide is generally structured as an anti-resonant reflecting optical waveguide (ARROW).

42. A system as recited in claim 34, wherein the non-solid core has a substantially square cross-section.

43. A system as recited in claim 34, wherein the non-solid core has a substantially rectangular cross-section.

44. A system as recited in claim 34, wherein the non-solid core has a substantially semicircular cross-section.

45. A system for making parallel optical measurements, comprising:
    (a) an optical waveguide comprising a generally planar solid-state material and a plurality of parallel channels within said solid-state material, including a Fabry-Perot reflector adjacent to each channel, whereby light injected into said channels is substantially prevented from leaking out of said channels in a transverse direction, and wherein said plurality of channels are elevated on a substrate as pedestal-like ridges above one topmost layer of said solid state material lateral to said channel;
    (b) means for injecting through each of said channels a sample material having an index of refraction which is lower than the index of refraction of the surrounding solid-state material;
    (c) a perpendicular waveguide portion for use in injecting light into the channels in a direction which is generally perpendicular to the orientation of said channels and the flow of said sample materials; and
    (d) means for measuring selected optical properties associated with the sample materials.

46. A system as recited in claim 45, wherein said selected optical properties include transmission, absorption, interference or fluorescence characteristics associated with said sample materials over macroscopic distances within the channel.

47. A system as recited in claim 45, wherein said solid state material is recessed lateral to said channel.

48. An integrated optical tweezers device for use in controlling the placement of small sample particles, comprising:
    an optical waveguide comprising a tapered channel surrounded by a solid-state material, including a Fabry-Perot reflector adjacent to said tapered channel, wherein said channel is elevated on a substrate on a pedestal-like ridge above one topmost layer of said solid state material lateral to said channel, and whereby light, once injected, is substantially prevented from leaking out of said channel in a transverse direction, and wherein at least one dimension of said tapered channel is tapered so as to create designed light intensity gradients within said channel.

49. A device as recited in claim 48, wherein said solid state material is recessed lateral to said channel.

50. A device as recited in claim 48, further comprising means for injecting into said channel a sample material having an index of refraction which is lower than the index of refraction of the surrounding solid-state material.

51. A device as recited in claim 48, further comprising means for injecting light into said tapered channel, wherein the injected light is guided within the channel and through the sample material.

52. A device as recited in claim 48, wherein said light intensity gradients are designed to exert a holding force on small particles of micron or sub-micron size.

53. A device as recited in claim 48, and further comprising a perpendicular waveguide portion for use in injecting light into said channel in a direction which is substantially perpendicular to a longitudinal axis of said tapered channel.

54. A device as recited in claim 48, and further comprising:
    means for injecting into said channel a sample material having an index of refraction which is lower than the index of refraction of the sunounding solid-state material;
    means for injecting light into said tapered channel, wherein the injected light is guided within the channel and through the sample material; and
    a perpendicular waveguide portion for use in injecting light into said channel in a direction which is substantially perpendicular to a longitudinal axis of said tapered channel; and
    wherein said light intensity gradients are designed to exert a holding force on small particles of micron or sub-micron size.

* * * * *